US009320728B2

(12) United States Patent
Yoshizaki et al.

(10) Patent No.: US 9,320,728 B2
(45) Date of Patent: Apr. 26, 2016

(54) METHOD FOR PRODUCING PATCH, PATCH AND PACKAGE (71) Applicant: HISAMITSU PHARMACEUTICAL CO., INC., Tosu-shi (JP)

(72) Inventors: Takahito Yoshizaki, Tosu (JP); Kouji Tanaka, Tosu (JP); Kazunosuke Aida, Tsukuba (JP); Terumitsu Kaiho, Chiyoda-ku (JP); Nobuo Tsutsumi, Chiyoda-ku (JP)

(73) Assignee: HISAMITSU PHARMACEUTICAL CO., INC., Tosu-shi (JP)

( * ) Notice: Subject to any disclaimer, the term of this patent is extended or adjusted under 35 U.S.C. 154(b) by 0 days.

(21) Appl. No.: 14/317,976

(22) Filed: Jun. 27, 2014

(65) Prior Publication Data

US 2015/0004215 A1    Jan. 1, 2015

(30) Foreign Application Priority Data

Jun. 28, 2013 (JP) .............................. JP2013-137147

(51) Int. Cl.
*A61K 31/4045* (2006.01)
*A61K 9/70* (2006.01)

(52) U.S. Cl.
CPC ........... *A61K 31/4045* (2013.01); *A61K 9/7053* (2013.01)

(58) Field of Classification Search
None
See application file for complete search history.

(56) References Cited

U.S. PATENT DOCUMENTS

| | | | |
|---|---|---|---|
| 4,832,953 | A | 5/1989 | Campbell et al. |
| 5,308,621 | A | 5/1994 | Taylor et al. |
| 5,807,570 | A | 9/1998 | Chen et al. |
| 5,906,830 | A | 5/1999 | Farinas et al. |
| 6,221,383 | B1 | 4/2001 | Miranda et al. |
| 8,802,134 | B2 | 8/2014 | Higo et al. |
| 8,877,235 | B2 | 11/2014 | Aida et al. |
| 2004/0047893 | A1 | 3/2004 | Dohner et al. |
| 2004/0057985 | A1 | 3/2004 | Bracht |
| 2004/0096491 | A1 | 5/2004 | Tateishi et al. |
| 2004/0142024 | A1 | 7/2004 | Chono et al. |
| 2005/0031547 | A1 | 2/2005 | Tamarkin et al. |
| 2005/0260255 | A1 | 11/2005 | Terahara et al. |
| 2006/0165763 | A1 | 7/2006 | Ito et al. |
| 2007/0184097 | A1 | 8/2007 | Kurita et al. |
| 2008/0038328 | A1 | 2/2008 | Higo et al. |
| 2008/0226698 | A1 | 9/2008 | Tang et al. |
| 2010/0034838 | A1 | 2/2010 | Staniforth et al. |
| 2011/0028880 | A1 | 2/2011 | Uchida et al. |
| 2011/0165247 | A1 | 7/2011 | Breitenbach |
| 2011/0195109 | A1 | 8/2011 | Michinaka et al. |
| 2012/0090275 | A1 | 4/2012 | Uchida et al. |
| 2013/0165875 | A1 | 6/2013 | Choi et al. |
| 2014/0112974 | A1 | 4/2014 | Takagi et al. |
| 2014/0170205 | A1 | 6/2014 | Uchida et al. |
| 2014/0186428 | A1 | 7/2014 | Aida et al. |

FOREIGN PATENT DOCUMENTS

| | | |
|---|---|---|
| CA | 2857156 | 6/2013 |
| EP | 0 304227 A2 | 2/1989 |
| EP | 1 074251 A1 | 2/2001 |
| EP | 1 366762 A1 | 12/2003 |
| EP | 1 547589 A1 | 6/2005 |
| EP | 2561865 A2 | 2/2013 |
| EP | 2749274 A1 | 7/2014 |
| JP | 63-093714 | 4/1988 |
| JP | 11/506462 | 6/1999 |
| JP | 2000-505061 A | 4/2000 |
| JP | 2001-518058 | 10/2001 |
| JP | 2002/504070 | 2/2002 |
| JP | 2004-83519 A | 3/2004 |
| JP | 2004-83523 A | 3/2004 |
| JP | 2006-169238 A | 6/2006 |
| JP | 2007516265 | 6/2007 |
| JP | 2009-518376 | 5/2009 |
| JP | 2010-521525 A | 6/2010 |
| WO | 96/39136 | 12/1996 |
| WO | 97/10812 | 3/1997 |
| WO | 97/11696 | 4/1997 |
| WO | WO 01/07018 A1 | 2/2001 |
| WO | WO 2008/115371 A2 | 9/2008 |
| WO | 2009/107478 A1 | 9/2009 |

(Continued)

OTHER PUBLICATIONS

EESR, Office Action issued Aug. 8, 2014 in EP Patent Application No. 14174708.9-1460.
Marcel Dekker, "Pharmaceutical skin penetration enhancement," edited by KA Walters and J. Hadgraft, (The United States), vol. 59, 1993, pp. 243-267. For example Japanese Patent Application Publication No. Sho 63-93714.
Official Action issued Jul. 2, 2015, in U.S. Appl. No. 14/123,148.
Japanese Office Action issued Jan. 23, 2013 in Patent Application No. 2012-267026 with English Translation.
"Basic Course in Drug Development XI", Second impression of the first edition, Apr. 20, 1974, pp. 424-427 and additional page (with English translation).

(Continued)

*Primary Examiner* — Sue Liu
*Assistant Examiner* — Thor Nielsen
(74) *Attorney, Agent, or Firm* — Oblon, McClelland, Maier & Neustadt, L.L.P.

(57) ABSTRACT

A method for producing a patch comprising a support layer and an adhesive agent layer arranged on at least one surface of the support layer, the method comprising:
step A) obtaining an adhesive agent layer composition comprising free ropinirole in an amount which results in a content of 5 to 13.2% by mass in an obtained adhesive agent layer;
step B) heating the adhesive agent layer composition at a temperature in a range from 50 to 76° C. for 5 minutes to 24 hours; and
step C) cooling the heated adhesive agent layer composition to normal temperature at an average rate of temperature drop of 1 to 20° C./hour, thereby obtaining the adhesive agent layer comprising the free ropinirole at a supersaturated concentration in a dissolved form.

9 Claims, 2 Drawing Sheets

(56) References Cited

FOREIGN PATENT DOCUMENTS

| WO | 2009107479 | 9/2009 |
| WO | 2010123103 | 10/2010 |
| WO | WO 2011/136283 A1 | 11/2011 |
| WO | 2012/165254 A1 | 6/2012 |
| WO | 2012/165253 A1 | 12/2012 |
| WO | 2013/081102 A1 | 6/2013 |

OTHER PUBLICATIONS

"Pharmaceutical Skin Penetration Enhancement", Drugs and the pharmaceutical sciences, vol. 59, 1993, pp. 243-267 and cover pages.

Office Action issued Aug. 19, 2013 in Japanese Patent Application No. 2013-137147 (with partial English-language translation).

Extended European Search Report issued Oct. 9,2013 in Patent Application No. 13156572.3.

Extended European Search Report issued Aug. 13, 2013 in Patent Application No. 13173633.2.

Anna Rocco, et al., "Analysis of phytosterols in extra-virgin olive oil by nano-liquid chromatography", Journal of Chromatography A, XP002707964A, vol. 1216, No. 43, 2009, pp. 7173-7178.

International Search Report Issued Jul. 10,2012 in PCT/JP121063161 Filed May 23, 2012.

International Search Report Issued Jul. 10,2012 in PCT/JP121063160 Filed May 23, 2012.

METHOD FOR PRODUCING PATCH, PATCH AND PACKAGE

BACKGROUND OF THE INVENTION

1. Field of the Invention

The present invention relates to a method for producing a patch, a patch and a package. More specifically, the present invention relates to a method for producing a patch using ropinirole as a drug and a patch and a package obtained by the method.

2. Related Background Art

Conventionally, the oral administration method using a tablet, a capsule, a syrup, or the like has been known as a drug administration method. In recent years, the transdermal administration method has been studied in which a drug is transdermally administered by using a patch. The method using a patch can solve problems associated with the oral administration method, and has advantages such as reduction in frequency of administration, improvement in compliance, and ease of administration and discontinuation. For these reasons, the transdermal administration method is expected as a drug administration method useful especially in a case of elderly or child patients.

The stratum corneum of the normal skin has a barrier function of preventing foreign substances from entering the body. Because of the barrier function, the use of conventional patches often ends up with insufficient transdermal absorption of the formulated drug ingredient. Moreover, since the stratum corneum is highly lipophilic, the skin penetrability of a drug is extremely low, in general.

In a generally known method for enhancing the skin penetrability of a drug in the transdermal administration method, the drug is contained at a supersaturated concentration in a transdermal preparation, and the difference in concentration gradient of the drug is utilized, as described in "Pharmaceutical Skin Penetration Enhancement," edited by K A Walters and J Hadgraft, (the United States), Vol. 59, Marcel Dekker, 1993, pp. 243-267. For example, Japanese Patent Application Publication No. Sho 63-93714 (Patent Literature 1) describes a patch comprising an adhesive agent layer containing a drug at a supersaturated concentration. However, the method in which a drug is contained at a supersaturated concentration in an adhesive agent layer of a patch involves an increased possibility of crystal precipitation of the drug. Hence, the method has problems associated with the crystal precipitation, such as reduction in cohesiveness and adhesion of the adhesive agent layer and reduction in skin penetrability due to a reduced drug release rate. Furthermore, Patent Literature 1 describes melting of crystals of the drug precipitated during storage by heating before use. However, such a method requires the heating operation every time the patch is used, and hence has problems in terms of convenience and ease of administration.

Moreover, studies have been recently made on transdermal administration of pharmaceutical preparations containing ropinirole, which is a drug useful for treating Parkinson's disease, restless legs syndrome, etc. and/or pharmaceutically acceptable salts thereof. For example, International Application Japanese-Phase Publication No. 2009-518376 (Patent Document 2) lists ropinirole as a drug contained in a composition for local administration. International Application Japanese-Phase Publication No. 2001-518058 (Patent Document 3) and International Application Japanese-Phase Publication No. Hei 11-506462 (Patent Document 4) disclose a transdermal pharmaceutical preparation comprising a support layer and a layer containing ropinirole. However, each of the patches described in Patent Documents 2 to 4 has such a problem that the skin penetrability of ropinirole is still insufficient, and hence it is difficult to keep the plasma concentration of ropinirole at a sufficiently high level. Moreover, each of the patches described in Patent Documents 2 to 4 has a problem of insufficient stability over time of ropinirole.

In addition, as a patch having excellent skin penetrability and stability of ropinirole, for example, International Publication No. WO 2009/107478 (Patent Document 5) describes a patch in which an adhesive agent layer contains free ropinirole formed by a reaction of an acid addition salt of ropinirole with a metal-ion containing desalting agent. International Publication No. WO 2012/165253 (Patent Document 6) describes a patch in which an adhesive agent layer contains a specific amount of ropinirole and/or a pharmaceutically acceptable salt thereof.

SUMMARY OF THE INVENTION

However, the present inventors have found that, even in a patch in which free ropinirole is stably contained as described in Patent Document 5 or 6, precipitation of crystals of free ropinirole may be caused with the lapse of time depending on the conditions under which the patch is produced such as the conditions for mass production or the like, and hence a better long-term storability is required. Particularly in cold districts such as those influenced by the Great East Japan Earthquake, or under harsh conditions where no storage facility is present, the problem of the crystal precipitation tends to come to the surface, and a higher level of long-term storability is required.

In this respect, the present inventors have conducted study for further improvement. As a result, the present inventors have found that, when ropinirole and/or a pharmaceutically acceptable salt thereof is used as a drug, a trace amount of crystals of the drug may precipitate in an adhesive agent layer during production depending on the production conditions of a patch, and these crystals serve as nucleus to cause the above-described crystal precipitation with the elapse of time.

The present invention has been made in view of the problems of the conventional technologies, and an object of the present invention is to provide a method for producing a patch using ropinirole as a drug, a patch and a package obtained by the method. Here, the method is capable of producing a patch which comprises free ropinirole at a supersaturated concentration in a dissolved form in an adhesive agent layer, can be stored for a long period even under harsh conditions where no storage facility is present as in the case of the aftermath of the Great East Japan Earthquake, and can achieve both skin penetrability and pharmaceutical physical properties at high levels.

The present inventors have conducted earnest study to achieve the above object, and consequently found the following fact. Specifically, in a method for producing a patch using ropinirole as a drug, an adhesive agent layer composition containing a specific amount of free ropinirole is prepared, and the adhesive agent layer composition is heated at a temperature in a range from 50 to 76° C., and then gently cooled at a specific rate of temperature drop. In such a case, the concentration of free ropinirole can be supersaturated, and free ropinirole can be contained in the adhesive agent layer in a completely dissolved form, even when the concentration of free ropinirole is a supersaturated concentration.

The present inventors have also found that astonishingly the thus obtained patch achieves a high level of skin penetrability as well as high levels of pharmaceutical physical properties such as adhesion and cohesiveness, even when crystals of a pharmaceutically acceptable salt of ropinirole is contained in the adhesive agent layer.

Furthermore, it has been found that such a patch can also achieve a high level of long-term storability, and can be stored for a long period even under harsh conditions where no storage facility is present as in the case of the aftermath of the Great East Japan Earthquake, and that the excellent skin penetrability and the pharmaceutical physical properties as described above are retained because no crystal of free ropinirole precipitation occurs for a long period. These findings have led to the completion of the present invention.

Specifically, a method for producing a patch of the present invention is as follows.

[1] A method for producing a patch comprising a support layer and an adhesive agent layer arranged on at least one surface of the support layer, the method comprising:

step A) obtaining an adhesive agent layer composition comprising free ropinirole in an amount which results in 5 to 13.2% by mass relative to a total mass of an obtained adhesive agent layer;

step B) heating the adhesive agent layer composition at a temperature in a range from 50 to 76° C. for 5 minutes to 24 hours; and step C) cooling the heated adhesive agent layer composition to normal temperature at an average rate of temperature drop of 1 to 20° C./hour, thereby obtaining the adhesive agent layer comprising the free ropinirole at a supersaturated concentration in a dissolved form.

[2] The method for producing a patch according to [1], wherein the adhesive agent layer composition further comprises at least one compound selected from the group consisting of benzyl alcohol, oleyl alcohol, octyldodecanol, and dimethyl isosorbide in an amount of 5 to 50 parts by mass relative to 100 parts by mass of the free ropinirole.

[3] The method for producing a patch according to [1] or [2], wherein the adhesive agent layer composition further comprises at least one compound selected from the group consisting of isopropyl myristate, isopropyl palmitate, lauryl alcohol, glycerin monooleate, propylene glycol monolaurate, polyoxyethylene sorbitan monooleate, and lauric acid diethanolamide in an amount of 10 to 150 parts by mass relative to 100 parts by mass of the free ropinirole.

[4] The method for producing a patch according to any one of [1] to [3], wherein the adhesive agent layer composition further comprises a rubber-based adhesive agent in an amount which results in 15 to 35% by mass relative to the total mass of the obtained adhesive agent layer.

[5] The method for producing a patch according to any one of [1] to [4], wherein the adhesive agent layer composition further comprises a pharmaceutically acceptable salt of ropinirole.

[6] The method for producing a patch according to [5], wherein sodium hydroxide is further blended in the adhesive agent layer composition, the amount of the sodium hydroxide being 0.5 to 1.2 moles per mole, in terms of free ropinirole, of the blended pharmaceutically acceptable salt of ropinirole.

[7] The method for producing a patch according to any one of [1] to [6], further comprising, after the step A and before the step B, step D1) applying the adhesive agent layer composition obtained in the step A onto the at least one surface of the support layer.

[8] The method for producing a patch according to any one of [1] to [6], further comprising, after the step B and before the step C, step D2) applying the heated adhesive agent layer composition obtained in the step B onto the at least one surface of the support layer.

A patch of the present invention is a patch obtained by the method for producing a patch according to any one of [1] to [8], the patch comprising the support layer and the adhesive agent layer arranged on the at least one surface of the support layer, wherein the adhesive agent layer contains the free ropinirole in an amount of 5 to 13.2% by mass, and the free ropinirole is contained at a supersaturated concentration in a dissolved form.

A package of the present invention is a package comprising:

a packaging container;

the patch of the present invention; and an oxygen absorber, wherein the patch and the oxygen absorber are tightly sealed together in the packaging container.

Note that although it is not exactly clear why the object can achieved by the present invention, the present inventors speculates as follows. Specifically, in the method for producing a patch of the present invention, first, the adhesive agent layer composition comprising free ropinirole is obtained, the adhesive agent layer composition is held within a specific temperature range of from 50 to 76° C., to thereby completely dissolve crystals and crystallization nuclei of the free ropinirole, even if present. Subsequently, the adhesive agent layer composition is gently cooled at an average rate of temperature drop of 1 to 20° C./hour. Thus, free ropinirole can be contained in a completely dissolved form in the adhesive agent layer, even when the concentration of the free ropinirole is a supersaturated concentration. Furthermore, this state can be retained stably for a long period.

Moreover, according to the method for producing a patch of the present invention, free ropinirole is contained in the adhesive agent layer at supersaturation in a dissolved form as described above. Hence, even when crystals or crystallization nuclei of a ropinirole salt (a pharmaceutically acceptable salt of ropinirole) are not completely dissolved but contained in the adhesive agent layer, the concentration equilibrium of the drug is retained. In addition, since the crystals or crystallization nuclei of the ropinirole salt are uniformly dispersed, crystal growth from the crystals or crystallization nuclei of the ropinirole salt is also suppressed. The present inventors speculate that, because of those reasons, the high level of skin penetrability and the high levels of pharmaceutical physical properties such as adhesion and cohesiveness are retained for an extremely long period.

In contrast, the dissolving (melting) conditions of the drug are not controlled sufficiently in conventional methods for producing a patch. The present inventors speculate that, for this reason, it is difficult to make the adhesive agent layer contain stably the drug at a supersaturated concentration in a completely dissolved form, and a trace amount of crystals of the drug remain or precipitate, and serve as nucleus to cause crystal precipitation with the elapse of time. In addition, drugs are generally distributed in the form of salts from the viewpoint of stability. Here, the melting points of ropinirole salts are extremely high (for example, about 244° C. for ropinirole hydrochloride). Hence, if such a drug is tried to be dissolved at about the melting point of a salt of the drug, other components contained in the adhesive agent layer are decomposed, so that physical properties for a patch are impaired.

Note that, in the method for producing a patch of the present invention, free ropinirole can be contained in a completely dissolved form in the adhesive agent layer also by conducting such a step of dissolving crystals after the crystals are precipitated in the adhesive agent layer composition and on a surface thereof.

In addition, the principle underlying the method for producing a patch of the present invention can be also applied to patches using drugs other than ropinirole. By making the adhesive agent layer contain a drug in the free form at a supersaturated concentration in a dissolved form, a high level of skin penetrability and high levels of pharmaceutical physical properties can be retained for a long period, even when crystals or crystallization nuclei of a pharmaceutically acceptable salt of the drug are contained in the adhesive agent layer or even when the conditions are severe. Examples of such a drug include those listed below as the drugs other than free ropinirole.

Note that, in the present invention, the phrase "a drug at a supersaturated concentration" means that the drug is present in the adhesive agent layer in an amount not smaller than the saturated solubility in the adhesive agent layer at room temperature (preferably 25° C.). When the drug is a salt, the concentration of the drug refers to a concentration obtained by converting the mass of the salt to the mass of the drug in the free form. For example, in the case of free ropinirole according to the present invention, a supersaturated concentration means that free ropinirole is present in the adhesive agent layer in an amount not smaller than the saturated solubility of free ropinirole in the adhesive agent layer. Moreover, in the present invention, dissolution of a drug refers to a state where the drug is scattered in a molecular state in a solvent (the adhesive agent layer, the adhesive agent layer composition, or the like). In addition, whether the drug is in a dissolved form can be checked by the fact that an endothermic melting point peak attributable to crystals is observed in differential scanning calorimetry (DSC). For example, when the drug is free ropinirole, the endothermic melting point peak (melting point) can be determined from a peak observed in a thermogram obtained by conducting a DSC measurement in which crystals of the drug (free ropinirole) are heated by using a differential scanning calorimeter from −90° C. to 80° C. at a rate of temperature rise of 10° C./min. In addition, for example, when the drug is ropinirole hydrochloride, the endothermic melting point peak (melting point) can be determined from a peak observed in a thermogram obtained by conducting a DSC measurement in which crystals of the drug (ropinirole hydrochloride) are heated by using a differential scanning calorimeter from −90° C. to 260° C. at a rate of temperature rise of 10° C./min.

The present invention makes it possible to provide a method for producing a patch using ropinirole as a drug, a patch and a package obtained by the method. Here, the method is capable of providing a patch which comprises free ropinirole at a supersaturated concentration in a dissolved form in a adhesive agent layer, can be stored for a long period even under harsh conditions where no storage facility is present as in the case of the aftermath of the Great East Japan Earthquake, and can achieve both skin penetrability and pharmaceutical physical properties at high levels.

Moreover, according to the production method of the present invention, it is possible to provide a patch and a package of the patch, in which even when crystals or crystallization nuclei of a pharmaceutically acceptable salt of ropinirole are contained in the adhesive agent layer, the crystal growth from the crystals or crystallization nuclei is sufficiently suppressed, and a high level of skin penetrability and high levels of pharmaceutical physical properties can be retained for a long period.

DETAILED DESCRIPTION OF THE PREFERRED EMBODIMENTS

Hereinafter, the present invention will be described in detail based on preferred embodiments thereof.

A method for producing a patch of the present invention is a method for producing a patch comprising a support layer and an adhesive agent layer arranged on at least one surface of the support layer, the method comprising:

step A) obtaining an adhesive agent layer composition comprising free ropinirole in an amount which results in a content of 5 to 13.2% by mass in an obtained adhesive agent layer;

step B) heating the adhesive agent layer composition at a temperature in a range from 50 to 76° C. for 5 minutes to 24 hours; and step C) cooling the heated adhesive agent layer composition to normal temperature at an average rate of temperature drop of 1 to 20° C./hour, thereby obtaining the adhesive agent layer comprising the free ropinirole at a supersaturated concentration in a dissolved form.

The method for producing a patch of the present invention is a method for producing a patch comprising a support layer and an adhesive agent layer arranged on at least one surface of the support layer. The support layer according to the present invention is not particularly limited, as long as the support layer is capable of supporting the adhesive agent layer. A stretchable or non-stretchable support layer can be used as the support layer according to the present invention. Examples of materials of the support layer include synthetic resins such as polyethylene terephthalate, polyethylene, polypropylene, polybutadiene, ethylene-vinyl acetate polymer, polyvinyl chloride, polyester, nylon, and polyurethane, as well as paper materials. Examples of the form of the support layer include films, sheets, laminates thereof; porous films; foamed articles; and woven fabrics and nonwoven fabrics.

Moreover, a thickness of the support layer according to the present invention is not particularly limited, and the thickness is preferably in a range from 5 to 1000 µm. If the thickness of the support layer is less than the lower limit value, ease of operation tends to be reduced, when the obtained patch is applied. Meanwhile, if the thickness of the support layer exceeds the upper limit value, ease of production tends to be reduced in the production process of the patch, as exemplified by difficulty in cutting the support layer or the patch.

Moreover, the patch obtained by the production method of the present invention may further comprise a release sheet on a surface of the adhesive agent layer opposite to the surface facing the support layer. Specific examples of the release sheet include films of polyesters such as polyethylene terephthalate, polyvinyl chloride, polyvinylidene chloride, and the like; laminate films of woodfree paper and polyolefin; and the like. These release sheets are preferably subjected to a releasing treatment such as a silicone coating on a surface to be in contact with the obtained adhesive agent layer, from the viewpoint that ease of operation is increased in peeling the release sheet from the patch.

<Step A>

The method for producing a patch of the present invention comprises a step A of obtaining an adhesive agent layer composition comprising free ropinirole in an amount which results in a content of 5 to 13.2% by mass in an obtained adhesive agent layer.

In the method for producing a patch of the present invention, free ropinirole is used as a drug. By the method for producing a patch of the present invention, the free ropinirole is contained at a supersaturated concentration in a dissolved form in the obtained adhesive agent layer. A content of the free ropinirole in the adhesive agent layer composition needs to be a content which results in an amount of supersaturation in the obtained adhesive agent layer, from the viewpoint that the obtained patch achieves a high level of skin penetrability of the drug. Specifically, in the present invention, the content of the free ropinirole in the adhesive agent layer composition has to be an amount which results in 5 to 13.2% by mass in the obtained adhesive agent layer, although the content cannot be generalized, because it depends on the constitution of the adhesive agent layer. In addition, the content is more preferably an amount which results in 8 to 13.2% by mass in the obtained adhesive agent layer. If the content of the free ropinirole is less than the lower limit, the skin penetrability of ropinirole of the obtained patch decreases, and a sufficient skin penetration amount cannot be retained for a long period, so that a plasma concentration of ropinirole cannot be retained at a high level. Meanwhile, if the content exceeds the upper limit, the free ropinirole is not completely dissolved in the adhesive agent layer, but crystals of the free ropinirole may be formed and precipitated out. In addition, the free ropinirole plasticizes the adhesive base agent, or degradation products (analogs) of ropinirole are formed. Hence, physical properties such as adhesion and/or skin penetrability of the drug tend to deteriorate.

Note that the content in the obtained adhesive agent layer in the present invention refers to a content relative to the entire mass of all the compounds actually contained in the adhesive agent layer obtained by the method for producing a patch of the present invention, and the entire mass of all the compounds actually contained in the adhesive agent layer is equivalent to a mass of non-volatile components in the adhesive agent layer composition, i.e., a mass obtained by subtracting a mass of volatile solvents from the total mass of the adhesive agent layer composition.

In the step A according to the present invention, the free ropinirole itself may be added to the adhesive agent layer composition. Alternatively, from the viewpoints of handleability and stability of the raw material, free ropinirole may be formed from a pharmaceutically acceptable salt of ropinirole in the adhesive agent layer composition, and the thus formed free ropinirole may be contained therein. Both methods may be employed in combination. A method for forming free ropinirole from a pharmaceutically acceptable salt of ropinirole (hereinafter referred to as ropinirole salt in some cases) is, for example, a method in which the ropinirole salt is desalted by blending the ropinirole salt and a metal-ion containing desalting agent (neutralizing agent) in the adhesive agent layer composition. The amount of the ropinirole salt blended is preferably such an amount that a content of free ropinirole in the obtained adhesive agent layer can be within the above-describe range.

The ropinirole salt is preferably an acid adduct, from the viewpoint that an acid adduct is easily desalted with the metal-ion containing desalting agent. Examples of the acid include monobasic acids such as hydrochloric acid, hydrobromic acid, and methanesulfonic acid; and polybasic acids such as fumaric acid, maleic acid, citric acid, and tartaric acid. One of these acids may be used alone, or two or more thereof may be used in combination. Of these acid adducts, the ropinirole salt is particularly preferably hydrochloric acid adduct (i.e., ropinirole hydrochloride).

Examples of the metal-ion containing desalting agent include metal hydroxides and the like. The metals include sodium, potassium, magnesium, and the like. One of these metal-ion containing desalting agents may be used alone, or two or more thereof may be used in combination. Of these metal-ion containing desalting agents, the metal-ion containing desalting agent is particularly preferably sodium hydroxide, from the viewpoints that sodium hydroxide is easy to handle during production, and that when sodium hydroxide is used in combination with a rubber-based adhesive agent (more preferably SIS), the stability over time of free ropinirole is further improved.

When the free ropinirole according to the present invention is formed from the ropinirole salt, the amount of the metal-ion containing desalting agent blended is preferably an amount of 0.5 to 4 equivalents to the ropinirole salt, in terms of acid-base equivalence. In addition, if the metal-ion containing desalting agent is blended in excess of the ropinirole salt in terms of acid-base equivalence, the stability over time of free ropinirole decreases, and large amounts of analogs of ropinirole are formed, so that the adhesive agent layer tends to be colored. In addition, the amount of the metal-ion containing desalting agent blended is more preferably 0.5 to 1.2 equivalents and further preferably 0.6 to 1.0 equivalents to the ropinirole salt in terms of acid-base equivalence from the following viewpoint. Specifically, when the amount is one equivalent or less, the amounts of ropinirole analogs formed tend to decrease, and the adhesive agent layer tends not to be colored particularly in a case where the metal-ion containing desalting agent is used in combination with a rubber-based adhesive agent (more preferably SIS). For example, when the ropinirole salt is desalted by blending the ropinirole salt and sodium hydroxide as the metal-ion containing desalting agent in the adhesive agent layer composition according to the present invention, the amount of sodium hydroxide blended is preferably 0.5 to 1.2 moles, and more preferably 0.6 to 1.0 moles per mole, in terms of free ropinirole, of the ropinirole salt blended.

In the present invention, the adhesive agent layer composition and/or the obtained adhesive agent layer may further comprise the ropinirole salt thus blended in the adhesive agent layer composition but remaining not converted to free ropinirole. In the present invention, the free ropinirole is contained in the adhesive agent layer at a supersaturated concentration in a dissolved form by the production method of the present invention. Thus, even when crystals or crystallization nuclei of a ropinirole salt are not dissolved but contained, crystal growth from these crystals or crystallization nuclei is suppressed, so that the high level of skin penetrability and the high levels of pharmaceutical physical properties such as adhesion and cohesiveness are retained for an extremely long period. When the adhesive agent layer composition according to the present invention contains the ropinirole salt, the content of the ropinirole salt is preferably an amount which results in 7.0% by mass or less, and more preferably an amount which results in 4.0% by mass or less, in terms of free ropinirole, relative to the total mass of the obtained adhesive agent layer. If the content exceeds the upper limit, it tends to be difficult to sufficiently suppress precipitation of and crystal growth from crystals and/or crystallization nuclei of the ropinirole salt.

In addition, in the present invention, the adhesive agent layer composition and/or the obtained adhesive agent layer may further comprise the metal-ion containing desalting agent and a metal salt formed by the desalting (neutralization). The metal salt is determined according to the combination of the ropinirole salt and the metal-ion containing desalting agent (neutralizing agent). The metal salt may be at least one selected from the group consisting of metal chlorides, metal bromides, metal iodides, and organic acid metal salts. More specific examples thereof include sodium chloride, calcium chloride, aluminum chloride, tin(II) chloride, iron(III) chloride, magnesium chloride, potassium chloride, sodium citrate, sodium oxalate, sodium tartrate, sodium bromide, and sodium succinate.

In addition, in the method for producing a patch of the present invention, drugs other than free ropinirole may be further incorporated in the adhesive agent layer composition, unless the effects of the present invention are impaired. Such drugs are not particularly limited, and examples thereof include hypnotic and sedative agents (flurazepam hydrochloride, rilmazafone hydrochloride, phenobarbital, amobarbital, medetomidine hydrochloride, dexmedetomine hydrochloride, and the like), antipyretic and antiinflammatory agents (butorphanol tartrate, perisoxal citrate, acetaminophen, mefenamic acid, diclofenac sodium, aspirin, alclofenac, ketoprofen, flurbiprofen, naproxen, piroxicam, pentazocine, indomethacin, felbinac, glycol salicylate, aminopyrine, loxoprofen, meloxicam, lornoxicam, and the like), steroidal antiinflammatory agents (hydrocortisone, prednisolone, dexamethasone, betamethasone, and the like), excitants and stimulants (methamphetamine hydrochloride, amphetamine hydrochloride, methylphenidate hydrochloride, and the like), neuropsychiatric drugs (imipramine hydrochloride, diazepam, sertraline hydrochloride, fluvoxamine maleate, paroxetine hydrochloride, citalopram hydrobromide, fluoxetine hydrochloride, alprazolam, haloperidol, clomipramine, amitriptyline, desipramine, amoxapine, maprotiline, mianserin, setiptiline, trazodone, lofepramine, milnacipran, duloxetine, venlafaxine, chlorpromazine hydrochloride, thioridazine, diazepam, meprobamate, etizolam, risperidone, asenapine maleate, and the like), hormone drugs (estradiol, estriol, progesterone, norethisterone acetate, metenolone acetate, testosterone, and the like), local anesthetics (lidocaine hydrochloride, procaine hydrochloride, tetracaine hydrochloride, dibucaine hydrochloride, propitocaine hydrochloride, and the like), agents for urinary organs (oxybutynin hydrochloride, tamsulosin hydrochloride, propiverine hydrochloride, imidafenacin, solifenacin succinate, tolterodine tartrate, and the like), skeletal muscle relaxants (tizanidine hydrochloride, eperisone hydrochloride, pridinol mesylate, suxamethonium chloride, and the like), agents for reproductive organs (ritodrine hydrochloride, meluadrine tartrate, and the like), antiepileptic agents (sodium valproate, clonazepam, carbamazepine, and the like), agents for autonomic nerves (carpronium chloride, neostigmine bromide, bethanechol chloride, and the like), antiparkinsonian agents (pergolide mesylate, bromocriptine mesylate, trihexyphenidyl hydrochloride, amantadine hydrochloride, talipexole hydrochloride, cabergoline, droxidopa, biperiden, selegiline hydrochloride, and the like), diuretic agents (hydroflumethiazide, furosemide, and the like), respiratory stimulants (lobeline hydrochloride, dimorpholamine, naloxone hydrochloride, and the like), antimigraine agents (dihydroergotamine mesylate, sumatriptan, ergotamine tartrate, flunarizine hydrochloride, cyproheptadine hydrochloride, and the like), antihistamines (clemastine fumarate, diphenhydramine tannate, chlorpheniramine maleate, diphenylpyraline hydrochloride, promethazine, and the like), bronchodilators (tulobuterol hydrochloride, procaterol hydrochloride, salbutamol sulfate, clenbuterol hydrochloride, fenoterol hydrobromide, terbutaline sulfate, isoprenaline sulfate, formoterol fumarate, and the like), cardiotonics (isoprenaline hydrochloride, dopamine hydrochloride, and the like), coronary vasodilators (diltiazem hydrochloride, verapamil hydrochloride, isosorbide dinitrate, nitroglycerin, nicorandil, and the like), peripheral vasodilators (nicametate citrate, tolazoline hydrochloride, and the like), smoking cessation aids (nicotine, varenicline tartrate, and the like), agents for circulatory organs (flunarizine hydrochloride, nicardipine hydrochloride, nitrendipine, nisoldipine, felodipine, amlodipine besilate, nifedipine, nilvadipine, manidipine hydrochloride, benidipine hydrochloride, enalapril maleate, temocapril hydrochloride, alacepril, imidapril hydrochloride, cilazapril, lisinopril, captopril, trandolapril, perindopril erbumine, atenolol, bisoprolol fumarate, metoprolol tartrate, betaxolol hydrochloride, arotinolol hydrochloride, celiprolol hydrochloride, carvedilol, carteolol hydrochloride, bevantolol hydrochloride, valsartan, candesartan cilexetil, losartan potassium, clonidine hydrochloride, and the like), antiarrhythmic agents (propranolol hydrochloride, alprenolol hydrochloride, procainamide hydrochloride, mexiletine hydrochloride, nadolol, disopyramide, and the like), anti-malignant-ulcer agents (cyclophosphamide, fluorouracil, tegafur, procarbazine hydrochloride, ranimustine, irinotecan hydrochloride, fluridine, and the like), antilipemic agents (pravastatin, simvastatin, bezafibrate, probucol, and the like), hypoglycemic agents (glibenclamide, chlorpropamide, tolbutamide, glymidine sodium, glybuzole, buformin hydrochloride, and the like), anti-peptic ulcer agents (proglumide, cetraxate hydrochloride, spizofurone, cimetidine, glycopyrronium bromide, and the like), cholagogues (ursodesoxycholic acid, osalmid, and the like), gastroprokinetic agents (domperidone, cisapride, and the like), hepatic disease agents (tiopronin and the like), anti-allergic agents (ketotifen fumarate, azelastine hydrochloride, emedastine difumarate, and the like), antiviral agents (acyclovir and the like), anti-vertigo agents (betahistine mesylate, difenidol hydrochloride, and the like), antibiotics (cephaloridine, cefdinir, cefpodoxime proxetil, cefaclor, clarithromycin, erythromycin, methylerythromycin, kanamycin sulfate, cycloserine, tetracycline, benzylpenicillin potassium, propicillin potassium, cloxacillin sodium, ampicillin sodium, bacampicillin hydrochloride, carbenicillin sodium, chloramphenicol, and the like), agents for habitual intoxication (cyanamide and the like), appetite suppressants (mazindol and the like), chemotherapeutic agents (isoniazid, ethionamide, pyrazinamide, and the like), blood coagulation accelerators (ticlopidine hydrochloride, warfarin potassium, and the like), anti-Alzheimer's agents (physostigmine, donepezil hydrochloride, tacrine, arecoline, xanomeline, galantamine hydrobromide, rivastigmine, and the like), serotonin receptor antagonist antiemetics (ondansetron hydrochloride, granisetron hydrochloride, ramosetron hydrochloride, azasetron hydrochloride, and the like), antigout agents (colchicine, probenecid, sulfinpyrazone, and the like), narcotic analgesics (morphine sulfate, morphine hydrochloride, codeine phosphate, cocaine hydrochloride, pethidine hydrochloride, and the like), antifungal agents (terbinafine hydrochloride, butenafine hydrochloride, amorolfine hydrochloride, neticonazole hydrochloride, miconazole nitrate, luliconazole, itraconazole, liranaftate, and the like), and the like. When such a drug other than free ropinirole is further incorporated, the amount of the drug incorporated is preferably an amount which results in a content of 20% by mass or less in the obtained adhesive agent layer, from the viewpoint that the obtained adhesive agent layer has better cohesiveness and better releasability of free ropinirole, although the preferable amount cannot be generalized because the amount varies depending on the purpose of the treatment.

The adhesive agent layer composition according to the present invention comprises the free ropinirole and at least an adhesive base agent. Examples of the adhesive base agent include rubber-based adhesive agents, acrylic-based adhesive agents, silicone-based adhesive agents, and the like. One of these adhesive base agents may be used alone, or two or more thereof may be used in combination. Of these adhesive base agents, at least one of the adhesive base agents is preferably a rubber-based adhesive agent, from the viewpoint that because of a strong cohesive force, the plasticizing effect of the free ropinirole on the adhesive base agent is suppressed.

Examples of the rubber-based adhesive agents include natural rubber and synthetic rubbers. The rubber-based adhesive agent is more preferably at least anyone selected from the group consisting of synthetic rubbers having neither hydroxy groups nor carboxyl groups such as styrene-isoprene-styrene block copolymer (hereinafter abbreviated as "SIS"), isoprene rubber, polyisobutylene (hereinafter abbreviated as "PIB"), styrene-butadiene-styrene block copolymer (hereinafter abbreviated as "SBS"), styrene-butadiene rubber (hereinafter abbreviated as "SBR"), and polybutene, from the viewpoint that formation of analogs of ropinirole can be suppressed sufficiently, and further the free ropinirole can be kept at a supersaturated concentration and in the dissolved form for a longer period, so that the stability over time of the free ropinirole is further improved. One of these rubber-based adhesive agents may be used alone, or two or more thereof may be used in combination. It is particularly preferable to use SIS alone, or a combination of SIS and PIB in a range of the mass ratio (mass of SIS:mass of PIB) of 9:1 to 1:1, from the viewpoint that such a rubber-based adhesive agent has a preferred cohesive force, and exhibits preferred adhesive force in the patch, and particularly when used in combination with sodium hydroxide, further improves the stability over time of ropinirole.

When the adhesive agent layer composition according to the present invention comprises the rubber-based adhesive agent, the content thereof is preferably an amount which results in 15 to 35% by mass relative to the total mass of the obtained adhesive agent layer. If the content is less than the lower limit, it is difficult to give sufficient cohesive force to the adhesive agent layer containing the free ropinirole at a supersaturated concentration in a dissolved form, and hence the adhesive base agent tends to remain on the skin after the obtained patch applied to the skin is peeled off. Meanwhile, if the content exceeds the upper limit, the obtained adhesive agent layer tends to be so hard that the adhesion of the patch decreases.

Examples of the acrylic-based adhesive agents include those listed as adhesive agents in "Iyakuhin Tenkabutu Jiten (Encyclopedia of Pharmaceutical Additives) 2000 (edited by International Pharmaceutical Excipients Council Japan, first impression was published on Apr. 28, 2000)," such as acrylic acid-acrylic acid octyl ester copolymer, 2-ethylhexyl acrylate-vinylpyrrolidone copolymer solution, acrylic acid ester-vinyl acetate copolymer, 2-ethylhexyl acrylate-2-ethylhexyl methacrylate-dodecyl methacrylate copolymer, methyl acrylate-2-ethylhexyl acrylate copolymer resin emulsion, and acrylic-based polymer contained in acrylic resin alkanolamine solution. One of these acrylic-based adhesive agents may be used alone, or two or more thereof may be used in combination. Of these acrylic-based adhesive agents, commercially available ones such as DURO-TAK acrylic adhesive agent series (manufactured by Henkel AG & Co. KGaA) and EUDRAGIT series (manufactured by HIGUCHI INC.) are preferably used as the acrylic-based adhesive agent.

As the silicone-based adhesive agent, a polymer having an organopolysiloxane skeleton is preferably used. In addition, the polymer having an organopolysiloxane skeleton has hydroxy groups (for example, silanol groups), the hydroxy groups are more preferably at least partially capped with trimethylsilyl groups. In addition, the polymer having an organopolysiloxane skeleton further preferably has adhesion. Note that the capping with trimethylsilyl groups includes capping in which a terminal silanol group of a polymer having an organopolysiloxane skeleton is end-capped with a trimethylsilyl group. Examples of the polymer having an organopolysiloxane skeleton include polydimethylsiloxane (such as a polymer represented by MQ in ASTM D-1418), polymethylvinylsiloxane (such as a polymer represented by VMQ in ASTM D-1418), polymethylphenylsiloxane (such as a polymer represented by PVMQ in ASTM D-1418), and the like. One of these polymers may be used alone, or two or more thereof may be used in combination.

When the adhesive agent layer composition according to the present invention comprises the acrylic-based adhesive agent and/or the silicone-based adhesive agent, the total content thereof (the total of the content of the acrylic-based adhesive agent and the content of the silicone-based adhesive agent) is preferably an amount which results in 10 to 90% by mass, more preferably an amount which results in 15 to 80% by mass, and particularly preferably an amount which results in 20 to 70% by mass relative to the total mass of the obtained adhesive agent layer, from the viewpoints of excellent formability of the adhesive agent layer, and excellent skin penetrability of the active ingredient of the obtained patch.

In addition, the adhesive agent layer composition according to the present invention preferably further comprises at least one compound selected from the group consisting of benzyl alcohol, oleyl alcohol, octyldodecanol, and dimethyl isosorbide (hereinafter referred to as compound (A) in some cases). Of these compounds, it is more preferable to further comprise octyldodecanol. When such a compound (A) (especially octyldodecanol) is further contained, there is a tendency that the precipitation of crystals of free ropinirole can be further suppressed, and the free ropinirole can be kept in the state of a supersaturated concentration and a dissolved form for a longer period.

When the compound (A) is further contained in the adhesive agent layer composition, the content of the compound (A) is preferably 1 to 80 parts by mass, more preferably 5 to 50 parts by mass, and particularly preferably 10 to 40 parts by mass, relative to 100 parts by mass of the free ropinirole. If the content is less than the lower limit, the effect of further suppressing the precipitation of crystals of free ropinirole tends not to be exhibited. Meanwhile, if the content exceeds the upper limit, there is a tendency that the sufficient skin penetrability of the free ropinirole cannot be retained.

Moreover, the adhesive agent layer composition according to the present invention preferably further comprises at least one compound selected from the group consisting of isopropyl myristate, isopropyl palmitate, lauryl alcohol, glycerin monooleate (GMO), propylene glycol monolaurate (PGML), polyoxyethylene sorbitan monooleate (Tween 80), and lauric acid diethanolamide (LADA) (hereinafter referred to as compound (B) in some cases), from the viewpoint that the skin penetrability of free ropinirole of the obtained patch is further improved. Of these compounds, it is particularly preferable to further comprise isopropyl palmitate. In the present invention, when the compound (A) (especially octyldodecanol) is contained in the adhesive agent layer composition, the skin penetrability of free ropinirole of the obtained patch may decrease in some cases. However, when the compound (B) (especially isopropyl palmitate) is further contained in the adhesive agent layer composition, there is a tendency that the decrease in the skin penetrability is suppressed, and the skin penetrability of free ropinirole is retained at an extremely high level for a long period.

When the compound (B) is contained in the adhesive agent layer composition, the content of the compound (B) is preferably 5 to 200 parts by mass, more preferably 10 to 150 parts by mass, and particularly preferably 15 to 120 parts by mass, relative to 100 parts by mass of the free ropinirole. If the content is less than the lower limit, the effect of further improving the skin penetrability of free ropinirole tends not to be exhibited. Meanwhile, if the compound (B) is contained in an amount exceeding the upper limit, there is a tendency that further effect of improving the skin penetrability is not obtained, and the compound (B) bleed from the adhesive agent layer, so that the adhesive force of the obtained patch decreases.

In the present invention, the adhesive agent layer composition further preferably comprises the compound (A) and the compound (B), and particularly preferably contains octyldodecanol and isopropyl palmitate described above, from the viewpoints that the precipitation of crystals of free ropinirole is suppressed more sufficiently, that the skin penetrability of free ropinirole is further improved, and that the skin penetrability can be retained at an extremely high level for a longer period. The mixing ratio (mass of compound (A)/mass of compound (B)) between the compound (A) and the compound (B) is preferably 1/10 to 1/2. If the mixing ratio is within the above-described range, there is a tendency that the precipitation of crystals of free ropinirole is further suppressed, and a sufficient skin penetrability of free ropinirole can be retained.

If necessary, the adhesive agent layer composition according to the present invention may further comprise additives such as an adsorbent, tackifier, plasticizer, absorption enhancer, antioxidant, filler, fragrance, preservative, and ultraviolet absorber, unless an effect of the present invention is impaired. In addition, these additives may be blended in the adhesive agent layer composition in the step A, or may be blended after the step B and before the step C, which are described later.

The adsorbent adsorbs polar solvents such as water. If a metal salt remains in the adhesive agent layer composition in a case where the free ropinirole according to the present invention is formed from the ropinirole salt and the metal-ion containing desalting agent by the neutralization reaction, the metal salt tends to aggregate and grow as crystals in the presence of a polar solvent such as water. Hence, the adhesive agent layer composition preferably further comprises the adsorbent, from the viewpoint that the aggregation and growth of crystals of the metal salt are suppressed, or the crystals are uniformly dispersed.

The adsorbent only needs to be an inorganic and/or organic substance having moisture-absorbing characteristics, and is not particularly limited, unless an effect of the present invention is impaired. General examples of the adsorbent include, among the additives listed in "Iyakuhin Tenkabutu Jiten (Encyclopedia of Pharmaceutical Additives) 2000 (edited by International Pharmaceutical Excipients Council Japan, first impression was published on Apr. 28, 2000)," inorganic substances and organic substances which are described to have moisture-absorbing characteristics, moisture-proof characteristics, or adsorbing characteristics, as well as aminoalkyl methacrylate copolymers, zinc oxide, and the like, which are not listed in "Iyakuhin Tenkabutu Jiten 2000," but are known to have moisture-absorbing characteristics. One of these adsorbents may be used alone, or two or more thereof may be used in combination. Examples of the adsorbents include minerals such as talc, kaolin, and bentonite; silicon compounds such as fumed silica (Aerosil (registered trademark) etc.) and hydrated silica; metal compounds such as zinc oxide and dried aluminum hydroxide gel; weak acids such as lactic acid and acetic acid; saccharides such as dextrin; polymers such as polyvinylpyrrolidone, propylene glycol, aminoalkyl methacrylate copolymer, crospovidone, and carboxyvinyl polymer.

When the adhesive agent layer composition according to the present invention comprises the adsorbent, the content of the adsorbent is preferably an amount which results in 0.5 to 10% by mass relative to the total mass of the obtained adhesive agent layer. If the content is less than the lower limit, the obtained effect of suppressing the aggregation and growth of crystals of the metal salt and the obtained effect of uniformly dispersing the crystals tend to be insufficient. Meanwhile, if the content exceeds the upper limit, it tends to be difficult to apply the patch, because of decrease in adhesive force of the obtained adhesive agent layer.

Examples of the tackifier include rosin-based resins such as "ESTER GUM (trade name, manufactured by Arakawa Chemical Industries, Ltd.)", "HARIESTER (trade name, manufactured by Harima Chemicals Group, Inc.)", "PENTALYN (trade name, manufactured by Eastman Chemical Company)", and "FORAL (trade name, manufactured by Eastman Chemical Company)"; terpene-based resins such as "YS RESIN (trade name, manufactured by YASUHARA CHEMICAL CO., LTD)" and "PICCOLYTE (trade name, manufactured by Loos and Dilworth)"; petroleum resins such as "ARKON (trade name, manufactured by Arakawa Chemical Industries, Ltd.)", "REGALREZ (trade name, manufactured by Eastman Chemical Company)", "PICCOLASTIC (trade name, manufactured by Eastman Chemical Company)", "ESCOREZ (trade name, manufactured by Exxon Mobil Corporation)", "WINGTACK (trade name, manufactured by The Goodyear Tire & Rubber Company)", and "QUINTONE (trade name, manufactured by Zeon Corporation)"; and aromatic hydrocarbon resins such as phenol-based resins and xylene-based resins. One of these tackifiers may be used alone, or two or more thereof may be used in combination.

When the adhesive agent layer composition according to the present invention comprises the tackifier, the content of the tackifier is preferably an amount which results in 10 to 80% by mass, more preferably in an amount which results in 15 to 70% by mass, and further preferably an amount which results in 20 to 60% by mass, relative to the total mass of the obtained adhesive agent layer, in view of sufficient adhesive force of the obtained patch and local irritancy of the obtained patch during peeling.

Examples of the plasticizer include petroleum-based oils such as paraffinic process oil, naphthenic process oil, and aromatic process oil; squalane, squalene; vegetable-based oils such as olive oil, camellia oil, castor oil, tall oil, and peanut oil; dibasic acid esters such as dibutyl phthalate and dioctyl phthalate; liquid rubbers such as polybutene and liquid isoprene rubber; diethylene glycol, polyethylene glycol, propylene glycol, dipropylene glycol, and the like. One of these plasticizers may be used alone, or two or more thereof may be used in combination. The plasticizer is preferably liquid paraffin or liquid polybutene from the viewpoint that a preferred adhesive force can be provided to the obtained adhesive agent layer.

When the adhesive agent layer composition according to the present invention comprises the plasticizer, the content of the plasticizer is preferably an amount which results in 5 to 60% by mass, more preferably an amount which results in 5 to 50% by mass, and further preferably an amount which results in 7 to 40% by mass, relative to the total mass of the obtained adhesive agent layer, in view of retaining the sufficient adhesive force of the patch.

Examples of the absorption enhancer include aliphatic alcohols such as isostearyl alcohol; fatty acids such as capric acid; fatty acid derivatives; polyethylene glycol; and the like, excluding those listed as the compound (B). One of these absorption enhancers may be used alone, or two or more thereof may be used in combination. When the adhesive agent layer composition according to the present invention comprises the absorption enhancer, the content of the absorption enhancer is preferably an amount which results in 1 to 30% by mass, more preferably an amount which results in 3 to 20% by mass, and further preferably an amount which results in 5 to 15% by mass, excluding the content of the compound (B), relative to the total mass of the obtained adhesive agent layer, in view of a sufficient penetrability into tissues of the active ingredient in the patch as a pharmaceutical preparation, local irritancy, and the like.

Examples of the antioxidant include tocopherols, ester derivatives thereof, ascorbic acid, ascorbyl stearate, nordihydroguaiaretic acid, dibutylhydroxytoluene (hereinafter abbreviated as BHT), butylhydroxyanisole, and the like. One of these antioxidants may be used alone, or two or more thereof may be used in combination.

Example of the filler include aluminum hydroxide, calcium carbonate, magnesium carbonate; silicates such as aluminum silicate and magnesium silicate; silicic acid; barium sulfate, calcium sulfate; calcium zincate; zinc oxide, titanium oxide; and the like. Examples of the preservative include disodium edetate, tetrasodium edetate, ethyl paraoxybenzoate, propyl paraoxybenzoate, butyl paraoxybenzoate, and the like. Examples of the ultraviolet absorber include p-aminobenzoic acid derivatives, anthranilic acid derivatives, salicylic acid derivatives, coumarin derivatives, amino acid-based compounds, imidazoline derivatives, pyrimidine derivatives, dioxane derivatives, and the like.

When the adhesive agent layer composition according to the present invention comprises any ones of the antioxidant, the filler, the preservative, the flavor, and the ultraviolet absorber, the total of the contents thereof is preferably an amount which results in 5% by mass or less, more preferably an amount which results in 3% by mass or less, and further preferably an amount which results in 1% by mass or less, relative to the total mass of the obtained adhesive agent layer.

In the step A according to the present invention, a solvent may be further incorporated into the adhesive agent layer composition. Especially in a case where the adhesive agent layer composition is applied onto the support layer or the release sheet before the step B described later (in a case of a first method described later), the adhesive agent layer composition preferably further comprises an appropriate amount of a solvent, from the viewpoint that the contained compounds are sufficiently dissolved to obtain a homogeneous composition before the application. Examples of such a solvent include toluene, hexane, ethyl acetate, cyclohexane, heptane, butyl acetate, ethanol, methanol, xylene, isopropanol, and the like. One of these solvents may be used alone, or two or more thereof may be used in combination.

In the step A according to the present invention, the method for obtaining the adhesive agent layer composition is not particularly limited, and the adhesive agent layer composition comprising free ropinirole according to the present invention can be obtained, for example, by mixing together the free ropinirole and the adhesive base agent; or; the ropinirole salt, the metal-ion containing desalting agent and the adhesive base agent; and, if necessary; the compound (A), the compound (B), the solvent and the like. The mixing method is not particularly limited, and the mixing can be conducted by, for example, a method using a mixer, a mortar, or the like.

The mixing is conducted preferably until the adhesive agent layer composition becomes homogeneous. Especially in a case where the adhesive agent layer composition is applied onto the support layer or the release sheet following to the step A according to the present invention and prior to the step B described later (in the case of the first method described later), the mixing is conducted preferably until the compounds contained in the adhesive agent layer composition are sufficiently dissolved or dispersed, from the viewpoint that a more homogeneous adhesive agent layer composition is applied onto the support layer.

<Step B>

The method for producing a patch of the present invention comprises a step B of heating the adhesive agent layer composition at a temperature in a range from 50 to 76° C. for 5 minutes to 24 hours. Such a step B may be conducted before or after the step of applying the adhesive agent layer composition. In addition, such a step B may be conducted under a condition where neither crystals nor crystallization nuclei of free ropinirole are present in the adhesive agent layer composition. If crystals or crystallization nuclei of free ropinirole remain and/or precipitate with the elapse of time in the adhesive agent layer composition, the step B may be conducted after such precipitation. Hereinafter, the method further comprising, after the step A and before the step B, a step D1 of applying the adhesive agent layer composition obtained in the step A onto the at least one surface of the support layer (order of steps: A, D1, B, and C) is referred to as a first method, whereas the method further comprising, after the step B and before the step C, a step D2 of applying the heated adhesive agent layer composition obtained in the step B onto the at least one surface of the support layer (order of steps: A, B, D2, and C) is referred to as a second method.

(First Method)

In the first method, the adhesive agent layer composition obtained in the step A is applied onto the at least one surface of the support layer in the step D1, and then heated at a temperature in a range from 50 to 76° C. for 5 minutes to 24 hours in the step B.

Since the adhesive agent layer composition is first applied onto the support layer in the first method, the compounds contained in the adhesive agent layer composition are preferably sufficiently dissolved in the step A. For such a sufficient dissolution, the adhesive agent layer composition preferably comprises the solvent and the like. In the step D1, the adhesive agent layer composition may be applied onto both surfaces of the support layer. However, the adhesive agent layer composition is preferably applied onto any one of the surfaces of the support layer, from the viewpoint that the production can be achieved by a simpler process.

In addition, when the patch obtained by the production method of the present invention further comprises the release sheet, the adhesive agent layer composition obtained in the step A may be applied onto a surface of the release sheet instead of the support layer in the step D1, and then heated in the step B.

In the step D1, the application method is not particularly limited, and a method used in a conventional method for producing a patch can be employed as appropriate. Moreover, a thickness of the application is not particularly limited, and is preferably a thickness which results in a thickness of the obtained adhesive agent layer of about 20 to about 200 μm. The thickness is preferably a thickness which results in a mass per unit area of the obtained adhesive agent layer of 25 to 200 $g/m^2$, and more preferably a thickness which results in 25 to 180 $g/m^2$. If the thickness of the obtained adhesive agent layer is less than the lower limit, it tends to be difficult to retain a sufficient skin penetration amount of free ropinirole. Meanwhile, even when the thickness exceeds the upper limit, the persistence of the skin penetration amount of the free ropinirole is not improved further. In addition, since the thickness increases, the necessary amount of the ropinirole and/or the pharmaceutically acceptable salt thereof also increases, so that the production costs become relatively high, and a phenomena (remaining of the adhesive agent layer) tends to easily occur in which the adhesive agent layer remains attached to the skin after the detachment of the obtained patch.

When the adhesive agent layer composition contains the solvent, the first method preferably further comprises, following the step D1, a drying step of drying the applied adhesive agent layer composition to thereby remove the solvent.

In addition, the first method may further comprise, before the step B:

a laminating step of laminating the release sheet or the support layer on a surface of the applied or dried adhesive agent layer composition, the surface being opposite to the surface facing the support layer or the release sheet;

a cutting step of cutting a laminate comprising the support layer and/or the release sheet and the applied (preferably dried) adhesive agent layer composition into pieces with desired sizes; and a packaging step of packaging the pieces of the laminate into packaging containers.

In the cutting step, it is preferable to cut the laminate so that the area of an attachment surface per piece can be 0.5 to 100 $cm^2$. If the area is less than the lower limit, or exceeds the upper limit, the obtained patch tends to be difficult to handle. In addition, the packaging container is not particularly limited, and ones which can be generally used as packaging containers for patches can be used as appropriate. Examples of the packaging container include packaging pouches made of a plastic, packaging pouches made of a plastic on which a metal layer (for example, aluminum layer) is formed, and packaging pouches made of a metal (for example, packaging pouches made of aluminum). Specific examples thereof include pouch-shaped containers and molded containers made of metal foils such as aluminum foil; films with low oxygen permeability such as ethylene-vinyl alcohol copolymer films, metal (aluminum or the like) deposited plastic films, and ceramic (silicon oxide or the like) deposited plastic films; metals such as stainless steel; glass; and laminated films of any of these with a polyacrylonitrile film, a polyethylene film, a cellulose film, or the like.

A heating temperature in the step B according to the present invention needs to be in a range from 50 to 76° C. If the heating temperature is lower than the lower limit value, crystals of free ropinirole remain or precipitate in the obtained adhesive agent layer, so that free ropinirole cannot be contained at a supersaturated concentration in a dissolved form. Meanwhile, if the heating temperature exceeds the upper limit value, crystals of free ropinirole tends to precipitate in the subsequent cooling step and/or pharmaceutical physical properties such as adhesion and cohesiveness of the obtained patch deteriorate. In addition, the heating temperature is preferably in a range from 55 to 72° C., from the viewpoints that free ropinirole can be more efficiently contained at a supersaturated concentration in a dissolved form in the adhesive agent layer, that crystal precipitation of free ropinirole can be suppressed for a longer period, and further that better pharmaceutical physical properties tend to be achieved.

In addition, a heating time in the step B according to the present invention needs to be in a range from 5 minutes to 24 hours. If the heating time is shorter than the lower limit value, crystals of free ropinirole precipitate with the elapse of time in the obtained adhesive agent layer. Meanwhile, if the heating time exceeds the upper limit value, further increase in the effect of suppressing the crystal precipitation of free ropinirole cannot be expected by employing such a long heating time, and such a heating time is economically disadvantageous. In addition, the heating time is preferably 10 minutes to 12 hours, from the viewpoint that there are tendencies that free ropinirole can be more efficiently contained at a supersaturated concentration in a dissolved form in the adhesive agent layer, and that crystal precipitation of the free ropinirole can be suppressed for a longer period.

(Second Method)

In the second method, first, the adhesive agent layer composition obtained in the step A is heated at a temperature in a range from 50 to 76° C. for 5 minutes to 24 hours in the step B, and then the heated adhesive agent layer composition is applied onto the at least one surface of the support layer in the step D2.

In the second method, the step D2 is the same as the step D1, except that the heated adhesive agent layer composition obtained in the step B is used instead of the adhesive agent layer composition obtained in the step A. Note that, in the second method, the adhesive agent layer composition is first heated to melt the drug and the like. Hence, the solvent and the like do not necessarily need to be introduced into the adhesive agent layer composition in the step A. In addition, in the second method, the heating is preferably conducted with stirring from the viewpoint of obtaining a more homogeneous adhesive agent layer composition in which the compounds contained are sufficiently melted or dispersed. Moreover, the heating temperature and the heating time in the step B in the second method are the same as described above.

Moreover, when the patch of the present invention is produced by the second method, the laminating step mentioned in the first method may further be included after the step D2 and before the step C described later. On the other hand, when the above-described cutting step and packaging step are further conducted in the production of the patch of the present invention by the second method, these steps are preferably conducted after the step C described later.

The method for producing a patch of the present invention may be the first method or the second method. The first method is preferably employed from the viewpoint of ease of production. Moreover, the method for producing a patch of the present invention preferably further comprises the packaging step after the step D1 and before the step B, from the viewpoints of ease of production and stability of the pharmaceutical preparation.

<Step C>

The method for producing a patch of the present invention comprises a step C of cooling the heated adhesive agent layer composition to normal temperature at an average rate of temperature drop of 1 to 20° C./hour, thereby obtaining the adhesive agent layer comprising free ropinirole at a supersaturated concentration in a dissolved form. The average rate of temperature drop refers to a rate found from the following formula: $(T_H-T_C)/\Delta t$, where $T_H$ is a temperature at the heating, $T_C$ is a temperature after the cooling, and $\Delta t$ is a time taken for the cooling. In addition, the temperature $(T_C)$ after the cooling is not particularly limited, as long as the temperature is normal temperature. The temperature $(T_C)$ is preferably 3 to 30° C., and more preferably 5 to 25° C., in general.

Such an average rate of temperature drop needs to be in a range from 1 to 20° C./hour. If the average rate of temperature drop is less than the lower limit value, further increase in the effect of suppressing the crystal precipitation of the drug cannot be expected by decreasing the average rate of temperature drop, and moreover such an average rate is not economically preferable. Meanwhile, if the average rate of temperature drop exceeds the upper limit value, the free ropinirole cannot be contained in a dissolved form. In addition, the average rate of temperature drop is preferably 2 to 18° C./hour, and more preferably 3 to 13° C./hour, from the viewpoint that there are tendencies that the free ropinirole can be more efficiently contained at a supersaturated concentration in a dissolved form in the adhesive agent layer, and that crystal precipitation of the drug can be suppressed for a longer period.

In the step C according to the present invention, the adhesive agent layer comprising free ropinirole at a supersaturated concentration in a dissolved form can be obtained. In addition, the method for producing a patch of the present invention may further comprise the above-described laminating step, cutting step, and packaging step, and the like, if necessary.

The method for producing a patch of the present invention as described above makes it possible to obtain a patch of the present invention comprising the support layer, and the adhesive agent layer arranged on the at least one surface of the support layer, wherein
the adhesive agent layer contains the free ropinirole in an amount of 5 to 13.2% by mass, and
the free ropinirole is contained at a supersaturated concentration in a dissolved form.

In the patch of the present invention, more preferred contents of free ropinirole, and, the constitutions and contents of the adhesive base agent comprised in the adhesive agent layer are the same as described above. In addition, unless the effects of the present invention are impaired, the adhesive agent layer according to the present invention may further comprise the ropinirole salt, the metal-ion containing desalting agent, the drug other than free ropinirole, the compound (A), the compound (B), the additives, and the like, which are mentioned in the description of the method for producing a patch of the present invention. The contents of these components are the same as described above.

In the patch of the present invention, free ropinirole is contained at a supersaturated concentration in a dissolved form. Hence, excellent skin penetrability of the free ropinirole and excellent pharmaceutical physical properties such as adhesion and cohesiveness are achieved. Moreover, the patch of the present invention has an excellent long-term storability. Even in a long-term storage, crystals of free ropinirole do not precipitate, and the skin penetrability and the pharmaceutical physical properties are retained at high levels. Furthermore, even when crystals or crystallization nuclei of the ropinirole salt are contained in the adhesive agent layer, the crystal growth from the crystals or crystallization nuclei is sufficiently suppressed, and a high level of skin penetrability and high levels of pharmaceutical physical properties can be retained for a long period.

In addition, when the method for producing a patch of the present invention further comprises the packaging step, a package of the present invention can be obtained. In the package of the present invention, the patch of the present invention is tightly sealed in a packaging container together with an oxygen absorber. The patch of the present invention is preferably tightly sealed in the packaging container together with the oxygen absorber for a period from the production to the use thereof, from the viewpoint that the formation of analogs of ropinirole can be further effectively suppressed, so that the stability over time of ropinirole is further improved.

The packaging container is as described above. In addition, examples of the oxygen absorber include ones using iron powder, and ones mainly containing vitamin C. More specific examples thereof include AGELESS series (manufactured by Mitsubishi Gas Chemical Company, Inc.), PharmaKeep series (manufactured by Mitsubishi Gas Chemical Company, Inc.), and the like. The amount of the oxygen absorber can be adjusted, as appropriate, according to the mass of the patch, the material and capacity of the container, and the like, and the mass of the oxygen absorber is preferably such that the amount of oxygen absorbed by the oxygen absorber can be 2.0 µl or more.

EXAMPLES

Hereinafter, the present invention is described more specifically based on Examples and Comparative Examples. However, the present invention is not limited to Examples below at all. Note that DSC measurement and evaluation of patches were carried out by the following methods.

<Differential Scanning Calorimetry (DSC Measurement)>

Figure 1:
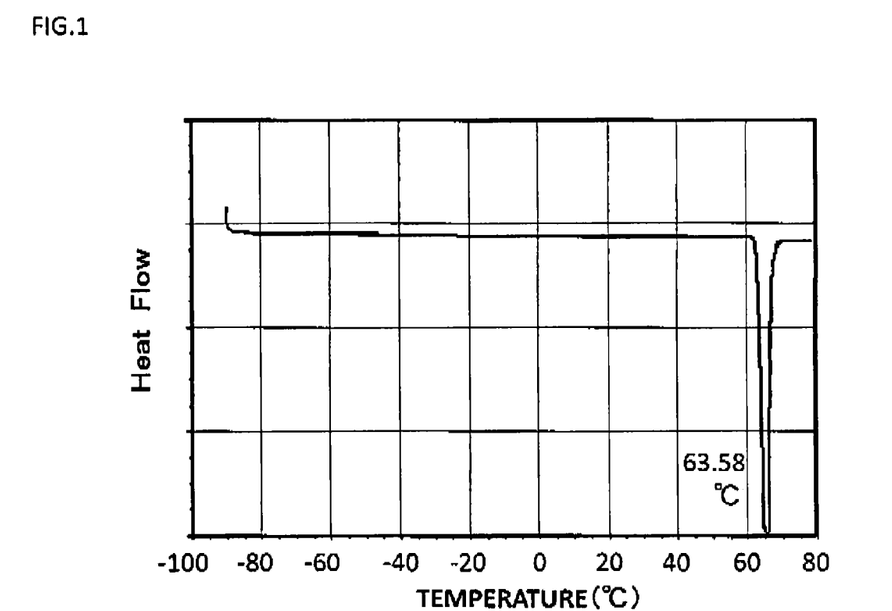
FIG. 1 is a graph showing a result of DSC measurement conducted on crystals of free ropinirole.

First, the melting point of crystals was determined. Specifically, DSC measurement was conducted in which crystals of free ropinirole was heated by using a differential scanning calorimeter ("Q-2000", manufactured by TA Instruments) from −90° C. to 80° C. at a rate of temperature rise of 10° C./min. From a peak observed in the obtained thermogram, the endothermic melting point peak (melting point) was determined to be 63.58° C. FIG. 1 shows a graph showing DSC measurement results of the crystals of free ropinirole. Moreover, ropinirole hydrochloride was subjected to DSC measurement by heating the adhesive agent layer from −90° C. to 260° C. at a rate of temperature rise of 10° C./min using the differential scanning calorimeter. Thus, the endothermic melting point peak (melting point) was determined to be 244° C.

Subsequently, the adhesive agent layer of each patch was subjected to DSC measurement by heating the adhesive agent layer from −90° C. to 260° C. at a rate of temperature rise of 10° C./min using the differential scanning calorimeter. Thus, the endothermic melting point peak at around 63.58° C. and 244° C. were observed.

On the basis of the obtained results of the DSC measurement, the following Free crystal evaluation and Salt crystal evaluation were conducted.

[Free Crystal Evaluation (Evaluation of Crystal Precipitation of Free Ropinirole)]

A: No endothermic melting point peak was observed at around 63.58° C.

B: An endothermic melting point peak was observed at around 63.58° C.

[Salt Crystal Evaluation (Evaluation of Crystal Precipitation of Ropinirole Hydrochloride)]

A: No endothermic melting point peak was observed at around 244° C.

B: An endothermic melting point peak was observed at around 244° C.

In addition, each patch in the packaging container was allowed to stand at a temperature of 25° C., and left for 24 months. The patch was also subjected to the Free crystal evaluation and the Salt crystal evaluation in the same manner as described above.

<Evaluation of Patches>

Patches obtained in Examples and Comparative Examples immediately after the production and patches which were allowed to stand in packaging containers at a temperature of 25° C. and left for 24 months after the production were subjected to the following Evaluation of appearance, Skin penetrability test, and Evaluation of pharmaceutical physical properties.

[Evaluation of Appearance]

A surface of the adhesive agent layer of each patch was observed with naked eyes, and a state of crystal precipitation was evaluated based on the following criteria:

A: no crystals were detected with any of the naked eyes,

B: crystals were detected with any of the naked eyes.

[Skin Penetrability Test]

First, dorsal skin was excised from a hairless mouse, and set to a Franz-type flow-through cell in which hot water of 32° C. was circulated through an outer peripheral portion thereof, with the dermis side being on the receptor chamber side. Next, each of the patches which were cut into a size of 5 cm$^2$ and from which the release sheets were removed was applied to the skin on the stratum corneum side. A phosphate buffered solution (PBS, phosphate buffered saline) of pH 7.4 was passed through the receptor chamber of the flow-through cell at a constant flow rate. A sample liquid was collected from the receptor chamber every 2 hours for 24 hours. The concentration of the drug (ropinirole) in each of the collected sample liquids was quantified by high-performance liquid chromatography, and the amount of the drug penetrating the skin was determined for each hour, and the maximum penetration rate (flux: μg/cm$^2$/hr) of the drug was calculated by using the following formula:

Flux (μg/cm$^2$/hr)=[drug concentration (μg/ml)×flow rate (ml)]/patch area (cm$^2$)/time (hr).

It can be understood that a pharmaceutical preparation having a large value of the maximum penetration rate was better in skin penetrability of the drug.

[Evaluation of Pharmaceutical Physical Properties]

Each of the patches obtained in Examples and Comparative Examples was measured for adhesive force with a probe tack tester and a peel tester and for cohesive force (holding power) with a creep-testing machine, and the pharmaceutical physical properties were evaluated based on the following criteria:

A: both the adhesive force and the cohesive force were sufficient,

B: at least one of the adhesive force and the cohesive force was insufficient.

Example 1

First, by using a mixing apparatus, 15.0 parts by mass (13.2 parts by mass in terms of free ropinirole) of ropinirole hydrochloride, 1.6 parts by mass of sodium hydroxide (a desalting agent, 0.8 moles per mole of the ropinirole hydrochloride), 11.9 parts by mass of liquid paraffin, toluene (solvent), 11.4 parts by mass of a styrene-isoprene-styrene block copolymer (SIS) (SIS 5000, manufactured by JSR), 42.6 parts by mass of an alicyclic hydrocarbon resin, 4.5 parts by mass of polyisobutylene, 10.0 parts by mass of isopropyl palmitate, and 3.0 parts by mass of octyldodecanol were mixed together. Thus, 100 parts by mass (the total mass of the compounds excluding the solvent (toluene)) of the adhesive agent layer composition was prepared. The constitution (excluding toluene) of the adhesive agent layer composition is shown in Table 1. Note that, at the above-described mole ratio of the ropinirole hydrochloride and sodium hydroxide, 2.6 parts by mass, in terms of free ropinirole, of ropinirole hydrochloride and 10.6 parts by mass of free ropinirole were contained in the adhesive agent layer composition. In addition, the amount of free ropinirole here was an amount which resulted in a supersaturated concentration in the adhesive agent layer composition (excluding the solvent).

Subsequently, the obtained adhesive agent layer composition was coated on a release sheet made of a film (made of polyethylene terephthalate) subjected to mold-release treatment with silicone, and the solvent was removed by drying. After that, a film made of polyethylene terephthalate as a support layer was laminated on the opposite surface of the dried adhesive agent layer composition from the release sheet, and this laminate was tightly sealed in a packaging pouch made of a laminated film having a polyacrylonitrile film as the innermost layer. Thus, a packaged article (a package) was obtained. Subsequently, the packaged article was heated to 50° C., and subjected to a heat treatment in which the packaged article was kept at the same temperature for 12 hours. Then, the packaged article was cooled to 25° C. over 3 hours (at an average rate of temperature drop of 8.3° C./hour). Thus, an intended patch comprising an adhesive agent layer was obtained in the packaging pouch. Note that the thickness of the adhesive agent layer in the obtained patch was a thickness which resulted in a mass per unit area of the adhesive agent layer of 100 g/m$^2$.

The patch immediately after production was subjected to the above-described Free crystal evaluation and Salt crystal evaluation. The patch was evaluated as A in the Free crystal evaluation and as B in the Salt crystal evaluation. Although crystals of ropinirole hydrochloride remained, crystals of free ropinirole were not observed. Hence, it was found that free ropinirole was contained in the adhesive agent layer at a supersaturated concentration in a dissolved form.

Examples 2 to 12

Figure 2:
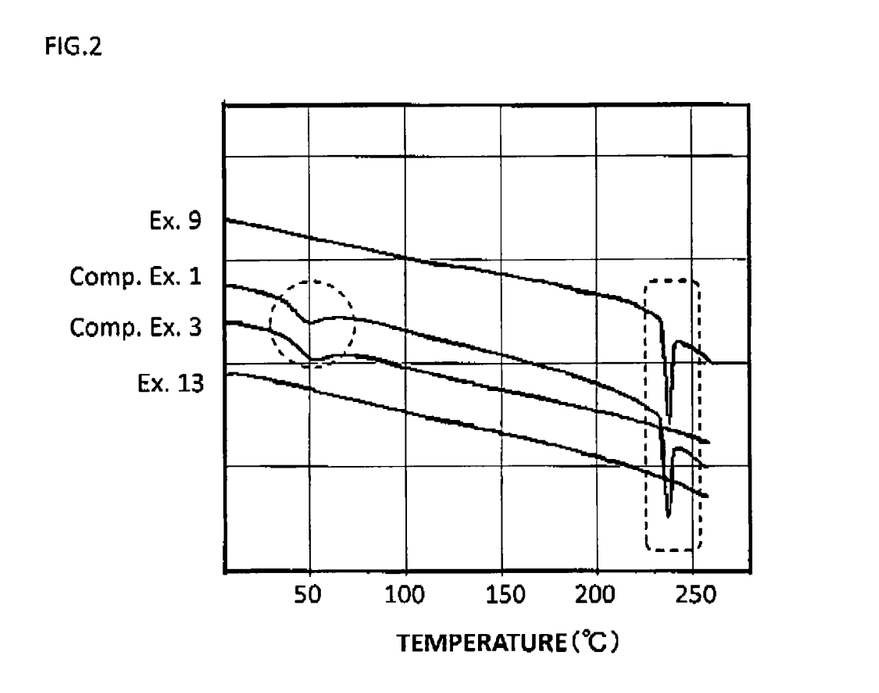
FIG. 2 is a graph showing results of DSC measurement conducted on the patches obtained in Examples 9, 13 and Comparative Examples 1, 2 immediately after production.

Patches were obtained in the same manner as in Example 1, except that the heat treatment conditions were changed to those shown in Table 2. The patches immediately after production were subjected to the above-described Free crystal evaluation and Salt crystal evaluation. Each of the patches was evaluated as A in the Free crystal evaluation and as B in the Salt crystal evaluation. It was found that although crystals of ropinirole hydrochloride remained, free ropinirole was contained in the adhesive agent layer at a supersaturated concentration in a dissolved form. FIG. 2 shows a graph showing the result of DSC measurement conducted on the patch obtained in Example 9 immediately after production.

Example 13

First, an adhesive agent layer composition was obtained in the same manner as in Example 1, except that the constitution shown in Table 1 was employed, in which the amount of sodium hydroxide added was 1.1 moles per mole of the ropinirole hydrochloride. Note that, at the above-described mole ratio between ropinirole hydrochloride and sodium hydroxide, ropinirole hydrochloride was not contained in the adhesive agent layer composition, and 13.2 parts by mass of free ropinirole was contained in the adhesive agent layer composition. In addition, the amount of free ropinirole here was an amount which resulted in a supersaturated concentration in the adhesive agent layer composition (excluding the solvent).

Subsequently, a patch was obtained in the same manner as in Example 1, except that the obtained adhesive agent layer composition was used, and the heat treatment conditions were changed to those shown in Table 2. The patch immediately after production was subjected to the above-described Free crystal evaluation and Salt crystal evaluation. The patch was evaluated as A in each of the Free crystal evaluation and the Salt crystal evaluation. It was found that, in the obtained patch, free ropinirole was contained in the adhesive agent layer at a supersaturated concentration in a dissolved form. Note that crystals of ropinirole hydrochloride were not observed. FIG. 2 shows a graph showing the result of DSC measurement conducted on the patch obtained in Example 13 immediately after production.

Example 14

First, an adhesive agent layer composition was obtained in the same manner as in Example 1, except that the constitution shown in Table 1 was employed, in which 13.2 parts by mass of free ropinirole was used instead of ropinirole hydrochloride and sodium hydroxide. In addition, the amount of free ropinirole here was an amount which resulted in a supersaturated concentration in the adhesive agent layer composition (excluding the solvent).

Subsequently, a patch was obtained in the same manner as in Example 1, except that the obtained adhesive agent layer composition was used, and the heat treatment conditions were changed to those shown in Table 2. The patch immediately after production was subjected to the above-described Free crystal evaluation and Salt crystal evaluation. The patch was evaluated as A in each of the Free crystal evaluation and the Salt crystal evaluation. It was found that, in the obtained patch, free ropinirole was contained in the adhesive agent layer at a supersaturated concentration in a dissolved form. Note that crystals of ropinirole hydrochloride were not observed.

Comparative Example 1

A patch in a packaging container was obtained in the same manner as in Example 1, except that the heat treatment was not conducted after the packaging, and the dried adhesive agent layer composition itself was used as the adhesive agent layer. The patch immediately after production was subjected to the above-described Free crystal evaluation and Salt crystal evaluation. The patch was evaluated as B in each of the Free crystal evaluation and the Salt crystal evaluation. It was found that crystals of ropinirole hydrochloride and crystals of free ropinirole were contained in the adhesive agent layer. FIG. 2 shows a graph showing the result of DSC measurement conducted on the patch obtained in Comparative Example 1 immediately after production.

Comparative Examples 2, 6 to 8

Patches were obtained in the same manner as in Example 1, except that the heat treatment conditions were changed to those shown in Table 2.

Comparative Example 3

A patch was obtained in the same manner as in Example 13, except that the heat treatment was not conducted after the packaging, and the dried adhesive agent layer composition itself was used as the adhesive agent layer. The patch immediately after production was subjected to the above-described Free crystal evaluation and Salt crystal evaluation. The patch was evaluated as B in the Free crystal evaluation and as A in the Salt crystal evaluation. It was found that crystals of ropinirole hydrochloride were not contained, but crystals of free ropinirole were contained in the adhesive agent layer. FIG. 2 shows a graph showing the result of DSC measurement conducted on the patch obtained in Comparative Example 3 immediately after production.

Comparative Examples 4, 9

Patches were obtained in the same manner as in Example 13, except that the heat treatment conditions were changed to those shown in Table 2.

Comparative Example 5

A Patch was obtained in the same manner as in Example 14, except that the heat treatment conditions were changed to those shown in Table 2.

TABLE 1

| Composition of adhesive agent layer composition (parts by mass) | Examples 1-12, Comparative Examples 1-2, 6-8 | Examples 13, Comparative Examples 3-4, 9 | Example 14, Comparative Example 5 |
|---|---|---|---|
| SIS | 11.4 | 11.2 | 12.4 |
| PIB | 4.5 | 4.4 | 5.5 |
| alicyclic hydrocarbon resin | 42.6 | 42.4 | 43.3 |
| liquid paraffin | 11.9 | 11.8 | 12.6 |
| isopropyl palmitate | 10.0 | 10.0 | 10.0 |
| octyldodecanol | 3.0 | 3.0 | 3.0 |
| ropinirole hydrochloride (parts by mass in terms of free ropinirole) | 15.0 (13.2) | 15.0 (13.2) | — |
| free ropinirole | — | — | 13.2 |
| sodium hydroxide | 1.6 | 2.2 | — |

Figure 3:
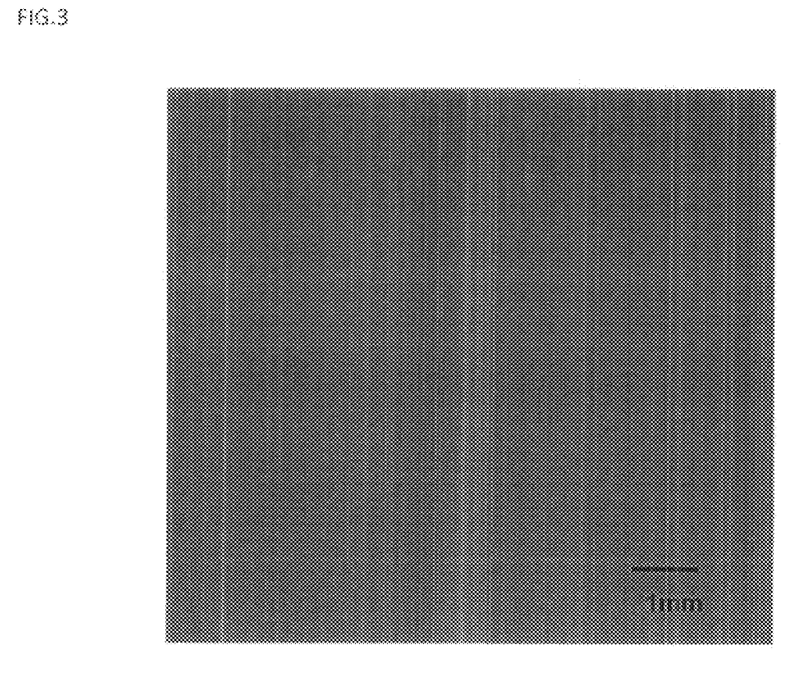
FIG. 3 is a photograph of the surface of the adhesive agent layer of the patch obtained in Example 9 allowed to stand for 24 months.
Figure 4:
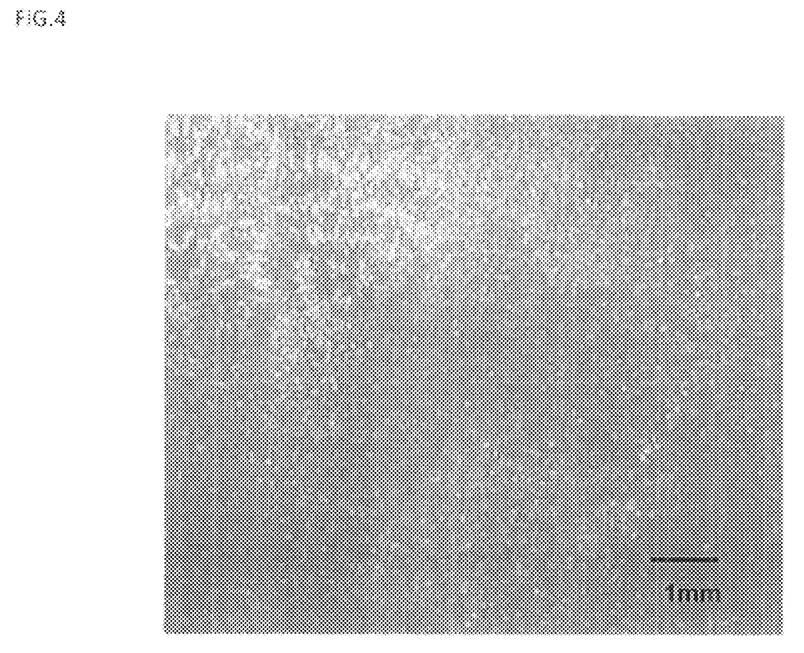
FIG. 4 is a photograph of the surface of the adhesive agent layer of the patch obtained in Comparative Example 1 and allowed to stand for 24 months.

Immediately after production and 24 months later, each of the patches obtained in Examples 1 to 14 and Comparative Examples 1 to 9 was subjected to the Evaluation of appearance, the Skin penetrability test, the Free crystal evaluation, the Salt crystal evaluation, and the Evaluation of pharmaceutical physical properties. In the Evaluation of appearance, the patches obtained in Examples 1 to 14 were evaluated as A, and retained their excellent appearance, even after 24 months had elapsed. On the other hand, the patches obtained in Comparative Examples 1 to 5 were evaluated as A in the Evaluation of appearance immediately after production, but 24 months later each of the patches was difficult to use as a pharmaceutical preparation, because it was obvious even under visual observation that crystals were precipitated on the surface of the adhesive agent layer. FIGS. 3 and 4 show photographs of surfaces of the adhesive agent layers of the patches obtained in Example 9 and Comparative Example 1 left for 24 months, respectively.

In addition, the Skin penetrability test showed that the patches obtained in Examples 1 to 14 retained excellent skin penetrabilities even after 24 months had elapsed, whereas the patches obtained in Comparative Examples 1 to 9 had insufficient skin penetrabilities. Moreover, the skin penetrabilities of the patches obtained in Comparative Examples 1 to 9 were further lowered with the advance of the crystal precipitation of free ropinirole and/or ropinirole hydrochloride, and the maximum skin penetration rates were lowered by 20% at the maximum, as compared with the patches obtained in Examples 1 to 14. Table 2 shows the results of the Free crystal evaluation, the results of the Salt crystal evaluation and the results of the Evaluation of Pharmaceutical Physical Properties, as well as the heating conditions in the production thereof.

TABLE 2

| | Heating conditions | | Free crystal evaluation/Salt crystal evaluation/ Evaluation of pharmaceutical physical properties | |
|---|---|---|---|---|
| | Heating temperature (° C.) | Heating time (Hours) | Immediately after production | 24 months later |
| Comp. Ex. 1 | No heat treatment | | B/B/A | B/B/B |
| Comp. Ex. 2 | 40 | 12 | B/B/A | B/B/B |
| Comp. Ex. 3 | No heat treatment | | B/A/A | B/A/B |
| Comp. Ex. 4 | 40 | 12 | B/A/A | B/A/B |
| Comp. Ex. 5 | 40 | 12 | B/A/A | B/A/B |
| Example 1 | 50 | 12 | A/B/A | A/B/A |
| Example 2 | 55 | 0.25(15 min) | A/B/A | A/B/A |
| Example 3 | 55 | 1 | A/B/A | A/B/A |
| Example 4 | 55 | 12 | A/B/A | A/B/A |
| Example 5 | 60 | 12 | A/B/A | A/B/A |
| Example 6 | 65 | 12 | A/B/A | A/B/A |
| Example 7 | 70 | 0.17(10 min) | A/B/A | A/B/A |
| Example 8 | 70 | 0.5(30 min) | A/B/A | A/B/A |
| Example 9 | 70 | 1 | A/B/A | A/B/A |
| Example 10 | 70 | 12 | A/B/A | A/B/A |
| Example 11 | 70 | 24 | A/B/A | A/B/A |
| Example 12 | 75 | 24 | A/B/A | A/B/A |
| Example 13 | 70 | 1 | A/A/A | A/A/A |
| Example 14 | 70 | 1 | A/A/A | A/A/A |
| Comp. Ex. 6 | 70 | 36 | A/B/B | A/B/B |
| Comp. Ex. 7 | 80 | 0.5(30 min) | A/B/B | A/B/B |
| Comp. Ex. 8 | 80 | 1 | A/B/B | A/B/B |
| Comp. Ex. 9 | 80 | 0.5(30 min) | A/A/B | B/B/B |

Comp. Ex.: Comparative Example

As is apparent from the results shown in Table 2, it was found that, in each of the patches obtained by the production method of the present invention, free ropinirole was contained in a dissolved form in the adhesive agent layer from the immediate period after the production, and that the crystal precipitation of free ropinirole was suppressed at a high level. Moreover, as is apparent from the results of the Skin penetrability test and the Evaluation of pharmaceutical physical properties, both a high level of skin penetrability and high levels of pharmaceutical physical properties were achieved in each of the patches of the present invention in which free ropinirole was contained at a supersaturated concentration in a dissolved form in the adhesive agent layer. Moreover, it was found that the skin penetrability and the pharmaceutical physical properties were retained even after long-term storage.

In addition, it was found that even when crystals or crystallization nuclei of a ropinirole salt were not completely dissolved but contained in the adhesive agent layer, each of the patches of the present invention retained a high level of skin penetrability and high levels of pharmaceutical physical properties such as adhesion and cohesiveness for an extremely long period, because crystal growth from these crystals or crystallization nuclei was suppressed.

As described above, the present invention makes it possible to provide a method for producing a patch using free ropinirole as a drug, and also to provide a patch and a package thereof obtained by the method. Here, the method is capable of producing a patch which comprises free ropinirole at a supersaturated concentration in a dissolved form in an adhesive agent layer, can be stored for a long period even under harsh conditions where no storage facility exists as in the case of the aftermath of the Great East Japan Earthquake, and can achieve both skin penetrability and pharmaceutical physical properties at high levels.

Moreover, according to the production method of the present invention, it is possible to provide a patch and a package of the patch, in which even when crystals or crystallization nuclei of a pharmaceutically acceptable salt of ropinirole are contained in the adhesive agent layer, the crystal growth from the crystals or crystallization nuclei is sufficiently suppressed, and a high level of skin penetrability and high levels of pharmaceutical physical properties can be retained for a long period.

What is claimed is:

1. A method for producing a patch comprising a support layer and an adhesive agent layer arranged on at least one surface of the support layer, the method comprising:
    A) obtaining an adhesive agent layer composition comprising
        free ropinirole in an amount which results in 5 to 13.2% by mass relative to a total mass of an obtained adhesive agent layer,
        at least one compound selected from the group consisting of benzyl alcohol, oleyl alcohol, octyldodecanol, and dimethyl isosorbide in an amount of 5 to 50 parts by mass relative to 100 parts by mass of the free ropinirole,
        at least one compound selected from the group consisting of isopropyl myristate, isopropyl palmitate, lauryl alcohol, glycerin monooleate, propylene glycol monolaurate, polyoxyethylene sorbitan monooleate, and lauric acid diethanolamide in an amount of 10 to 150 parts by mass relative to 100 parts by mass of the free ropinirole, and a rubber-based adhesive agent in an amount which results in 15 to 35% by mass relative to the total mass of the obtained adhesive agent layer;

B) heating the adhesive agent layer composition at a temperature in a range from 50 to 70° C. for 5 minutes to 24 hours; and C) cooling the heated adhesive agent layer composition to a normal temperature ranging from 3 to 30° C. at an average rate of temperature drop of 1 to 20° C./hour, thereby obtaining the adhesive agent layer comprising the free ropinirole at a supersaturated concentration in a dissolved form, wherein no precipitation of free ropinirole crystals occur within 24 months in the obtained adhesive agent layer at a temperature of 25° C.

2. The method for producing a patch according to claim 1, wherein the adhesive agent layer composition further comprises at least one compound selected from the group consisting of benzyl alcohol, oleyl alcohol, octyldodecanol, and dimethyl isosorbide in an amount of 10 to 40 parts by mass relative to 100 parts by mass of the free ropinirole.

3. The method for producing a patch according to claim 1, wherein the adhesive agent layer composition further comprises at least one compound selected from the group consisting of isopropyl myristate, isopropyl palmitate, lauryl alcohol, glycerin monooleate, propylene glycol monolaurate, polyoxyethylene sorbitan monooleate, and lauric acid diethanolamide in an amount of 15 to 120 parts by mass relative to 100 parts by mass of the free ropinirole.

4. The method for producing a patch according to claim 1, wherein the adhesive agent layer composition further comprises a pharmaceutically acceptable salt of ropinirole.

5. The method for producing a patch according to claim 4, wherein sodium hydroxide is further blended in the adhesive agent layer composition, the amount of the sodium hydroxide being 0.5 to 1.2 moles per mole, in terms of free ropinirole, of the blended pharmaceutically acceptable salt of ropinirole.

6. The method for producing a patch according to claim 1, further comprising, after the obtaining A and before the heating B, D1) applying the adhesive agent layer composition obtained in A onto the at least one surface of the support layer.

7. The method for producing a patch according to claim 1, further comprising, after the heating B and before the cooling C, D2) applying the heated adhesive agent layer composition obtained in B onto the at least one surface of the support layer.

8. A patch obtained by the method for producing a patch according to claim 1, the patch comprising the support layer and the adhesive agent layer arranged on the at least one surface of the support layer, wherein the adhesive agent layer comprises the free ropinirole in an amount of 5 to 13.2% by mass, and the free ropinirole is contained at a supersaturated concentration in a dissolved form.

9. A package comprising:
a packaging container;
the patch according to claim 8; and
an oxygen absorber, wherein
the patch and the oxygen absorber are tightly sealed together in the packaging container.

* * * * *